United States Patent [19]

Chen et al.

[11] Patent Number: 5,096,809

[45] Date of Patent: Mar. 17, 1992

[54] WHOLE BLOOD ASSAYS USING POROUS MEMBRANE SUPPORT DEVICES

[75] Inventors: Fon-Chiu M. Chen, San Diego; Eugene Fan, La Jolla, both of Calif.

[73] Assignee: Pacific Biotech, Inc., San Diego, Calif.

[21] Appl. No.: 223,520

[22] Filed: Jul. 25, 1988

[51] Int. Cl.⁵ .............................................. G01N 33/53
[52] U.S. Cl. .................................. 435/7.9; 436/518; 436/67; 436/178; 436/514; 422/55; 422/56; 422/58; 210/789
[58] Field of Search ............... 435/6, 7, 28; 422/55, 422/56; 436/67, 178, 514, 535; 210/789

[56] References Cited

U.S. PATENT DOCUMENTS

| | | | |
|---|---|---|---|
| 3,843,456 | 10/1974 | Haden et al. | 195/139 |
| 3,888,629 | 6/1975 | Bagshawe | 23/230 |
| 4,200,690 | 4/1980 | Root et al. | 435/7 |
| 4,212,742 | 7/1980 | Solomon et al. | 210/247 |
| 4,243,534 | 1/1981 | Bulbenko | 436/67 |
| 4,256,693 | 3/1981 | Kondo et al. | 422/56 |
| 4,376,110 | 3/1983 | David et al. | 436/513 |
| 4,424,279 | 1/1984 | Bohn et al. | 436/534 |
| 4,477,575 | 10/1984 | Vogel et al. | 436/170 |
| 4,594,327 | 6/1986 | Zuk | 436/514 |
| 4,637,978 | 1/1987 | Dappen | 435/11 |
| 4,654,197 | 3/1987 | Lilja et al. | 422/56 |
| 4,654,310 | 3/1987 | Ly | 436/164 |
| 4,657,850 | 4/1987 | Grieve | 435/7 |
| 4,670,381 | 6/1987 | Frickey et al. | 435/7 |

Primary Examiner—Christine Nucker
Assistant Examiner—Jeffrey Stucker
Attorney, Agent, or Firm—Knobbe, Martens, Olson & Bear

[57] ABSTRACT

Disclosed is a method for detecting analytes in samples of whole blood using solid-phase, permeable support assay devices. The whole blood assays require no steps or reagents other than those necessary to carry out the same analysis on plasma or serum using the devices. The color visualization of the analytical field on which the interpretation of the assay depends is not affected by the presence of intact erythrocytes or any degree of hemolysis in the blood sample.

17 Claims, 1 Drawing Sheet

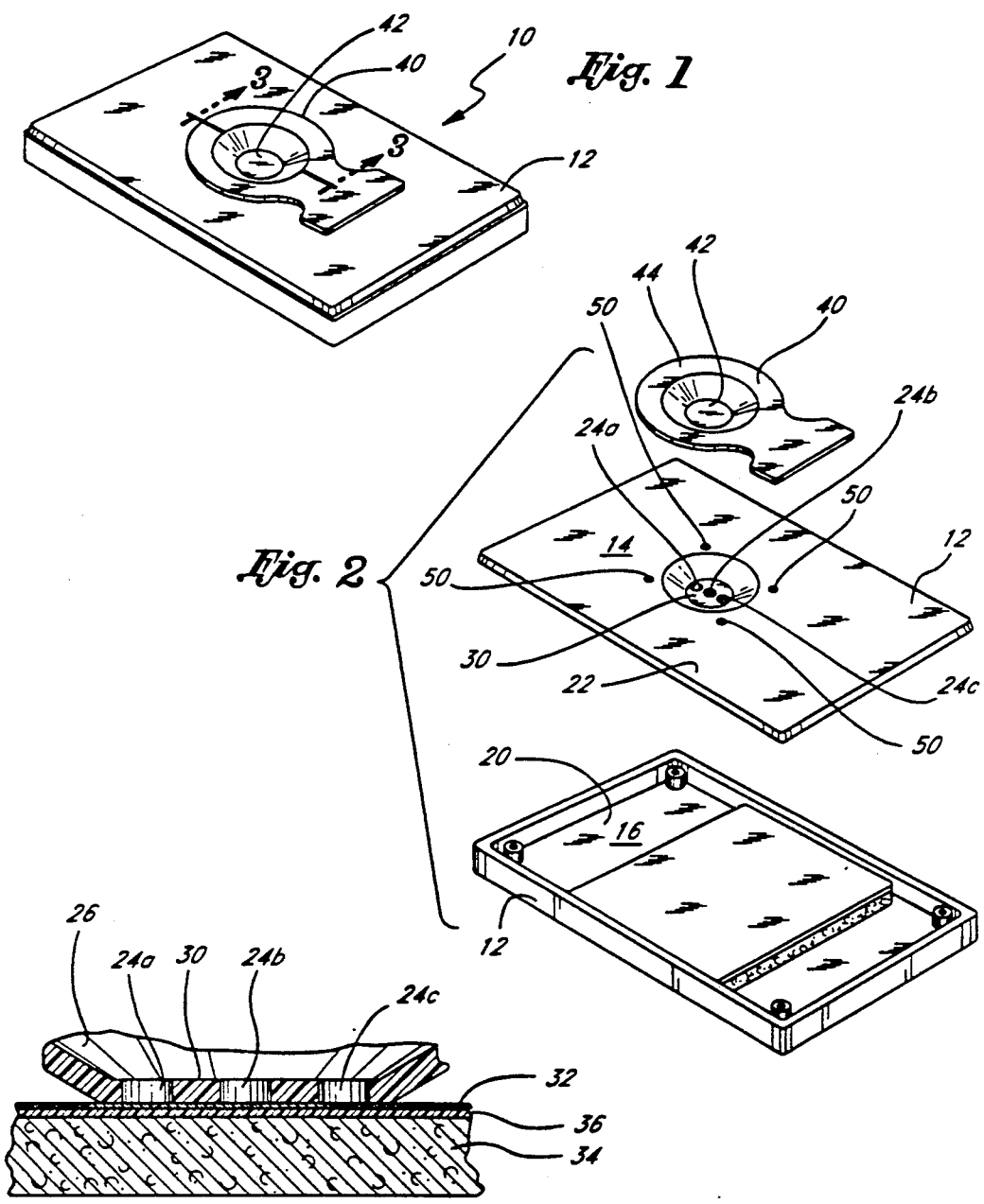

WHOLE BLOOD ASSAYS USING POROUS MEMBRANE SUPPORT DEVICES

BACKGROUND OF THE INVENTION

The present device relates to methods for analyzing whole blood using immunoassay and other assay devices in which a fluid is analyzed by contacting the fluid with a porous support on which are immobilized agents that selectively bind the analyte.

Devices that isolate analytes from solution by binding them to a solid porous support eliminate the need for precipitation and centrifugation, or filtration, and have made it possible to perform many diagnostic tests at home or in clinical settings where there are no laboratory facilities. However, the extra-laboratory application of these devices has not been fully realized because the interpretation of these "blood tests," like those of several other diagnostic methodologies, requires that they be carried out on blood serum or plasma, either of which must be separated from the cellular components of whole blood by centrifugation prior to the analysis.

The interpretation of porous support assays depends on the observance of color at the locus of the bound analyte where a chromogenic reaction occurs. If hemoglobin, the highly colored component of erythrocytes, stains the same field, an accurate observation is difficult or impossible. Not only hemoglobin, but also colorless insoluble components of blood can impair the assay. In addition, the cellular material of intact erythrocytes or their ruptured "ghosts" can reduce sensitivity of the test by blanketing analyte binding sites on membrane surfaces. Blood cells or cellular debris can alter test performance in yet another way by clogging membrane pores and restricting sample flow.

Some procedures of this type (e.g., Reflotron, Boehringer Mannheim Diagnostics, Indianapolis, IN.) have been adapted to whole blood analysis by providing a glass fiber prefilter which separates erythrocytes from whole blood by adhesion of the cells to the glass fibers. To achieve efficient erythrocyte separation and reliable assay results using a prefilter of this type, the blood must be tested within a few minutes after collection or else treated with an anticoagulant. Once the coagulation process has begun, contact with the large surface area of the glass fiber mat will accelerate fibrin clot formation, and the flow through the prefilter and porous membrane as well will be restricted. The glass fibers retain only intact erythrocytes; they will not retain hemoglobin from lysed red blood cells. There is some degree of hemolysis in all collected blood; some specimens, notably those of cord blood from infants, are virtually impossible to obtain in an unhemolyzed state, even with a careful collection. Thus, even with the use of a prefilter, hemoglobin staining from whole blood samples will contaminate the observed analytical field.

The extra-laboratory potential of many diagnostic tests could be fully realized if the separating properties of porous membrane assay devices could be applied to exclude cellular components of blood together with soluble hemoglobin in the process of isolating the analyte.

It is therefore an object of the invention to provide such a whole blood assay system and to define the physical and operating parameters of these assay systems which best achieve the desired result.

BRIEF SUMMARY OF THE INVENTION

The present invention provides a method for detecting an analyte in a sample of whole blood using a porous membrane support assay device.

In one embodiment of the invention, the method comprises the steps of providing an assay device comprising a liquid-permeable support layer having on its surface a means for detecting the presence of a selected analyte, applying a sample of whole blood to the layer, drawing the colored components of the blood through the layer, and then visually indicating on the layer the presence or absence of the analyte in the blood sample. In another embodiment of the invention, the method further comprises the step of lysing the red blood cells in the sample to release the colored components within and to permit the colored components to be drawn through the layer. In one variation, the lysing of the red blood cells is performed prior to applying the blood sample to the layer, and in another variation the lysing step is performed after applying the blood sample to the layer.

In any of the foregoing methods the layer may be a membrane and the drawings of the blood sample through the layer may be done by wicking liquid components of the blood away from the membrane, or by otherwise drawing the liquid away from the membrane, as through use of vacuum or centrifugation techniques.

In a preferred embodiment of the invention, the method further comprises the steps of adding a relatively colorless liquid to the layer after the blood sample has been applied and then drawing the relatively colorless liquid, together with the colored components of the blood sample, through the layer.

In embodiments of the invention in which the layer is a membrane, the membrane may have pores on average no greater than 25 $\mu$m in size. In a preferred embodiment, the membrane has pores on average no greater than 10 $\mu$m in size, and in a particularly preferred embodiment, the membrane has an average pore size of about 5 $\mu$m.

In one embodiment of the invention, the analyte and the means for detecting the analyte comprise a ligand-antiligand pair; in a preferred embodiment, the ligand-antiligand pair comprises an antigen and an antibody.

In an embodiment of the invention where the permeable support layer is a membrane and the means for detecting the analyte is immobilized thereon, the method may comprise further the steps of binding the analyte to the detecting means on the membrane, and inducing a color change on the membrane, wherein the color change is dependent on the binding of the analyte to the detecting means. In a preferred embodiment, the color change occurs as a result of the interaction of an enzyme with its substrate, when the enzyme is immobilized on the membrane at the time of the color change. In all embodiments of the invention the analyte and the means for detecting the analyte may comprise an enzyme-substrate pair. In any of the foregoing embodiments of the invention, the drawing step may comprise drawing hemoglobin from lysed cells through the support layer or alternatively may comprise drawing whole red blood cells through the layer.

One preferred embodiment of the invention is an infectious mononucleosis assay for use in analyzing whole blood samples. The analyte may advantageously be anti-mononucleosis antibody or mononucleosis antigen.

BRIEF DESCRIPTION OF THE DRAWINGS

FIG. 1 is a perspective view of a representative assay device.

FIG. 2 is an exploded perspective view of the assay device.

FIG. 3 is a cross section of a portion of the assay device of FIG. 1, taken along the line 3—3.

DETAILED DESCRIPTION OF THE INVENTION

A representative assay device 10 having a porous analytical field is shown in FIG. 1. The assay device 10 has a rectangular housing 12 which has a top 14 and a bottom 16. When assembled, a space is enclosed in the housing, so that the housing has an inside 20 and an outside 22.

The housing 12 has openings 24 that permit communication between the outside 22 of the housing and the inside 20 of the housing 12. In the illustrated device, these openings 24 comprise a first opening 24a, a second opening 24b, and a third opening 24c. Similar devices may have fewer openings or may have a greater number.

The illustrated device has a means 26, for receiving and holding a liquid sample, and distributing that sample through the openings 24. The sample receiving means 26 is a well formed in the top 14 of the housing 12, which tapers from top to bottom, so it can serve as a funnel for directing liquid into the openings 24.

As best illustrated in FIG. 3, each of the openings 24 has a layer of porous material 32 across the bottom of the opening 24 and visible through said opening. This porous support 32 is located so that liquid flowing from the sample receiving means 26 through the openings 24 must pass through the portion of the porous support 32 visible through the openings 24.

Located beneath the porous support 32 on the inside 20 of the housing 12 is absorbent material 34 which acts to draw fluid through the porous support 32. A layer of non-absorbent wicking material may be interposed between the porous support 32 and the absorbent material 34 to facilitate the transfer of liquid away from the porous support 32. A barrier layer 36 may also be provided between the porous material 32 and the absorbent material 36. The barrier material is dissolvable in the liquid sample and is adapted to prevent, for a predetermined period, the transfer of liquid from the porous support to the absorbent material, so that the sample remains longer in contact with the analytical surface.

The assay device 10 is constructed so that the bottom 30 of the sample receiving means 26 presses tightly against the combined thicknesses of the porous support 32 and the absorbent material 34 to prevent shifting of the porous support 32 with respect to the openings 24.

A prefilter 40 is fitted over the sample receiving means 26, and comprises a filter portion 42 at the base of an open shaped body portion 44 capable of holding a liquid sample and directing its flow through the filter portion 42. The filter portion 42 primarily filters out unwanted materials such as mucous or particulate matter but may also be provided with reagents that facilitate the assay process such as detergents or non-reactive protein which act to prevent non-specific binding and reduce background reactions. The base of the prefilter is in contact with the porous support 32 and acts to distribute the sample uniformly to the surface of the porous support 32.

The porous support 32 is a porous membrane to which reagents for the analysis of interest may be fixed either by chemical binding or physical impregnation. The analyte-specific reagent may occupy the entire visible surface of the membrane or it may be confined to a zone, which becomes the analytical field. These selectively binding agents can be a member of a ligand-antiligand pair, including for example, an enzyme, hormone receptor, or an RNA or DNA sequence. The representative example is an immunoassay device in which the porous support 32 is a porous nylon membrane to which antibody to the analyte has been bound.

In a typical assay procedure, a sample is loaded into the device, either on the prefilter or directly on the porous support and allowed to diffuse downwardly where analyte-specific antiligand immobilized on the membrane binds any analyte that is present. A conjugate molecule, made up of antiligand labelled with a detectable molecule, is added in solution and the conjugate binds the analyte bound to the membrane. The surface of the membrane is then washed free of unbound substances, and the label of the conjugate is identified, usually by a chromogenic reaction, so that the colored area of the membrane indicates the presence and concentation of analyte.

The results of the assay may be read as a qualitative, unreferenced visual observation, a semi-quantitative estimation using a color intensity comparison scale, or it may be read quantitatively by reflectance photometry.

In order to analyze whole blood samples in a reliable manner the porous support assay device and the protocol for assay performance should be designed so that in the process of analysis, the analytical field is substantially cleared of cells, cello fragments and hemoglobin staining before the final chromogenic step.

Theoretically, intact erythrocytes, containing hemoglobin, as well as cell fragments can be cleared by using a support membrane having a mean pore diameter greater than the mean diameter of erythrocytes. Erythrocytes have a mean diameter of 8 $\mu$m. Table 1 indicates that nylon membrane with pore sizes greater than this, at 10 $\mu$m and 20 $\mu$m do not retain these cells on their surfaces. There are two upper limitations on pore size, however. First, as the pore size is increased, the amount of membrane surface which becomes unavailable for binding analyte increases rapidly as the square of increasing pore diameter. For example, if pore diameter increases from 5 $\mu$m to 10 $\mu$m, the area of the analytical zone of the membrane not occupied by analyte binding ligand increases by $(10/5)^2$ or 4-fold (regardless of the shape of the pores). The effective binding area decreases in a corresponding way, the rate of decrease being a function of density of pore openings per area and accelerating with increasing pore diameter, as follows: Let $A_t$ = Total surface area of the membrane, $A_p$ = Pore area, and $A_f$ = Functional area = $A_t - A_p$ In the case of round pores, $A_p = A_t (n\pi r^2)$, where n = the number of pores per unit area, $A_t$.
Then $$A_f = A_t - A_t(n\pi r^2), = A_t(1-n\pi r^2)$$

The rate at which $A_f$ changes with r is expressed by the derivative, $$dA_f = -2n\pi r \cdot dr$$

and the relative change in the functional area is $$\frac{-dA_f}{A_f} = \frac{2n\pi r \, dr}{1 - n\pi r^2}$$

As r increases, the denominator becomes small much faster than the numerator becomes large, and the rate of decrease accelerates rapidly at large values of r and/or n. The relationship again holds regardless of the geometry of the pores.

Secondly, as pore size increase, the flow rate of a fluid through the membrane increases, and in order to keep the sample in contact with the membrane surface long enough for adequate binding of the analyte, it may be necessary to decrease the flow rate by increasing the barrier layer beneath the membrane.

Possibly, pore size need not always be so large for erythrocytes to pass through the membrane. The anatomy of the cell is that of a flexible biconcave disk and experimental data (Table 1) indicates that at least in some cases erythrocytes will pass through nylon membranes with mean pore sizes as small as 5 μm. The difference in erythrocytes exclusion between two membranes evaluated are presumably due to manufacturing variations in the thickness of the membranes, and diverse specifications for estimating pore size.

When analytical requirements indicate that membranes of small pore size membranes be used, the analytical field can be cleared of erythrocytes by lysing the cells so that the empty cells or their fragments can be flushed through the pore channels.

Erythrocytes can be lysed by several methods. They may be mechanically disrupted by passage through a fine needle (20 gauge or less) attached to a syringe or by Dounce homogenization. They may also be lysed by dilution of the blood sample into a hypotonic (effectively less than the physiological 0.15M) solution such as distilled water. In a hypotonic environment, the erythrocytes swell and rupture, releasing their contents and becoming a membrane "ghost." Alternatively, the integrity of the erythrocyte membrane can be destroyed by detergents and organic solvents which solubilize or extract the constituent lipids, or by enzymes, such as lipases which digest the phospholipids. A lysing step can be carried out prior to assaying the sample (examples A-2, A-3) or may occur in the course of the assay procedure with comparable results.

Hemoglobin from lysed erythrocytes can be removed from the membrane surface if it does not bind irreversibly to it and if the fluid volume following the sample is adequate to draw the color below the surface.

The examples demonstrate that the presence of intact erythrocytes or free hemoglobin in the sample does not interfere with the performance of the assay under the conditions routinely used for serum and plasma samples.

Clearing of Erythrocytes

In Examples A-1 and B-1 samples of whole blood treated with an anticoagulant were applied to the assay device either directly to the membrane (A-1) or through the prefilter (B-1). These samples, comprising mostly, intact erythrocytes, gave the appropriate positive assay response and the membrane at the time of observation was visually clear of either intact erythrocytes or hemoglobin.

Clearing of Hemoglobin

Hemoglobin in a whole blood sample from lysed cells does not bind irreversibly to the nylon membrane but the initial stain fades as it is washed away by liquid during the analytical process.

In examples A-2 and B-2, erythrocytes in samples of whole blood were partially lysed by simple mixing with 0.5% Tween-20 to provide a sample of mixed intact erythrocytes and free hemoglobin, and to determine the effect of these agents on the assay. These samples were applied both directly to the membrane (A-2) and through the prefilter (B-2). The sample volume was followed by the introduction of enzyme conjugate in a colorless solution containing a somewhat lower (0.1%) concentration of Tween-20 than the solution used to lyse the cells, and having the same volume as the lysed sample. A volume of 500 μl 0.5% Tween-20, again a colorless solution and in more than 3-fold the sample volume, followed by equal volume of substrate solution in 0.3M AMP buffer, provided a cumulative effective wash volume to clear the analytical field of hemoglobin as well as any intact cells. Since 0.5% Tween-20 is effective in partially lysing erythrocytes in a whole blood sample in 1 minute, a larger volume is effective in lysing any such cells remaining on the assay surface at the wash step.

Conjugate Binding in the Presence of Hemoglobin

In Examples A-3 and B-3 enzyme conjugate is mixed with the sample before it is applied to the membrane and partially lyses the cells, indicating that low (0.1%) Tween-20 acts effectively as an lysing agent. When this sample is applied to the device either directly (A-3) or through the prefilter (B-3), there is a positive assay response. The enzyme conjugate binds satisfactorily to analyte in the pretreatment of the whole blood sample, and since the substantial concentration of erythrocytes and hemoglobin present of do not inhibit this binding, any blood or hemoglobin remaining on the membrane surface when conjugate is added in the normal course of an assay will similarly not interfere with binding.

Native blood samples, that is those not treated with anticoagulant, may be successfully analyzed in the porous support device if the assay is performed within a few minutes after collection. Although it is not inconvenient to collect a blood sample directly into a chamber containing anti-coagulant, it may, in some instances, be preferable to transfer smaller volumes of blood, such as those collected from a finger, earlobe, or the heel of infants, directly into the assay device for immediate assay.

Whole blood samples may be similarly analyzed on porous support devices which employ other binding pairs, such as DNA probe assays, in assays using a chain of enzyme reactions to produce the color signal, such as a glucose or cholesterol assay or those that use conventional dipstick chemistries.

EXAMPLES

Detections of human chorionic gonadotropin (HCG) in whole blood samples were performed with reaction devices (A) without prefilter, (B) with prefilter, and (C)

with prefilter coated with detergent. The reaction device consists of rabbit anti-alpha-HCG antibody immobilized on a porous membrane support (Nylon 66, pore size of 5 μm, supplied by Micron Separation, Inc. (I4SI) together with several underlying layers of absorbent material to draw the fluid sample through. The membrane and absorbent material are encased in a plastic housing and the analytical surface of the membrane is exposed through an opening in the housing.

The enzyme conjugate solution in the following examples was alkaline phosphatase-conjugated mouse monoclonal anti-beta-HCG antibody in Tris buffer and 0.1% Tween-20. The substrate solution was 4 mM 3-indoxyl phosphate in 0.3M AMP Buffer.

An HCG-free whole blood sample with EDTA as anticoagulant or whole blood sample without anticoagulant (Example A-4) was spiked with a known amount of HCG to give a final concentration of 100 mIU/ml. This HCG-spiked whole blood sample was used for all the examples described below.

A. Reaction Device without Prefilter

1. Untreated whole blood sample

A 50 μl sample of HCG-containing EDTA-whole blood was applied directly to the membrane of the reaction device and was drawn through in approximately 2 minutes. Enzyme conjugate solution (150 μl) was then added and passed through the membrane in approximately 15 seconds. After an additional 2 minutes 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

2. Whole blood sample partially lysed before application on the membrane.

A 50 μl sample of HCG-containing EDTA-whole blood was mixed with 0.1 ml of 0.5% Tween to partially lyse the red blood cells. The mixture was then applied directly to the membrane of the reaction device and was drawn through in approximately 4 minutes. Enzyme conjugate solution (150 μl) was then added and passed through the membrane in approximately 20 seconds. After an additional 2 minutes 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

3. Whole blood sample reacted with enzyme conjugate prior to application on the membrane.

A 50 μl sample of HCG-containing EDTA-whole blood sample was mixed with 150 μl of enzyme conjugate, and incubated at room temperature for 1 minute. During this time the red blood cells were partially lysed. The reaction mixture was applied directly to the membrane of the reaction device and was drawn through in approximately 10 minutes. After an additional 2 minutes 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

4. Untreated whole blood without anticoagulant

A 50 μl sample of HCG-containing whole blood to which no anticoagulant had been added was applied directly to the membrane of the reaction device and was drawn through in approximately 30 seconds. Enzyme conjugate solution (150 μl) was then added and passed through the membrane in approximately 15 seconds. After an additional 2 minutes 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

B. Reaction Device with Glass-fiber Prefilter

The prefilter device consists of a glass-fiber (U6-40, pore size 6-40 μm, supplied by Pall Corporation) fitted into a plastic holder; the assembled prefilter was attached to the reaction device. The glass-fiber component of the prefilter was in direct contact with the porous membrane support on the reaction device.

1. Untreated whole blood sample

A 50 μl sample of HCG-containing EDTA-whole blood sample was applied to the glass-fiber prefilter of the device and was drawn through in approximately 1 minute. Enzyme conjugate solution (150 μl) was then added and passed through the membrane in approximately 25 seconds. After an additional 2 minutes the prefilter was removed and discarded. 500 μl of 0.5% Tween was added, and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

2. Whole blood sample partially lysed before application on the membrane.

A 50 μl HCG-containing EDTA-whole blood was mixed with 0.1 ml of 0.5% Tween to partially lyse the red blood cells. The mixture was then applied to the glass-fiber prefilter of the device and was drawn through in approximately 1 minute. Enzyme conjugate solution (150 μl) was then added and passed through the membrane in approximately 15 seconds. After an additional 2 minutes the prefilter was removed and discarded. 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

3. Whole blood sample reacted with enzyme conjugate prior to application to the device A 50 μl sample of HCG-containing EDTA-whole blood sample was mixed with 150 μl of enzyme conjugate, and incubated at room temperature for 3 minutes. During this time the red blood cells were partially lysed. The reaction mixture was applied to the glassfiber prefilter of the device and was drawn through in approximately 30 seconds. After an additional 2 minutes the prefilter was removed and discarded. 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

C. Reaction Device with Detergent-coated Glass-fiber Prefilter

The following procedure was used to coat the prefilter with detergent: About 25 pieces of 2.5 cm² round glassfiber (U6-40, pore size 6-40 μm, supplied by Pall Corporation) was mixed with 1 gm CHAPS (CHAPS: 3-[(3cholamidopropyl) dimethyl-ammonio]1-propanesulfonate) in a closed container and the container has rotated for 45 minutes to assure even coating. After coating, the excess CHAPS was removed from the glass-fiber by shaking it on a sieve device. A coated glass-fiber disk was mounted in the plastic holder, and the fully assembled prefilter was then attached to the reaction device as described previously.

1. Untreated whole blood sample

A 50 μl sample of HCG-containing EDTA-whole blood sample was applied to the glass-fiber prefilter of the device and was drawn through in approximately 3 minutes. Enzyme conjugate solution (150 μl) was then added and passed through the membrane in approximately 30 seconds. After an additional 2 minutes the prefilter was removed and discarded. 500 μl of 0.5% Tween was added and after it had passed through the membrane, 500 μl of substrate solution was added. Within 5 minutes a clear blue color spot appeared on that portion of the membrane coated with anti-alpha-HCG antibody, and the enzyme reaction was stopped by applying 500 μl of a 0.1% acetic acid solution to the membrane.

2. Whole blood sample partially lysed before application on the membrane.

A 50 μl sample of HCG-containing EDTA-whole blood was mixed with 0.1 ml of 0.5% Tween to partially lyse the red blood cells. The mixture was then applied to the glassfiber prefilter of the device and was drawn through in approximately 1 minute. Enzyme conjugate solution (150 μl) was then added and passed through the membrane in approximately 10 seconds. After an additional 2 minutes the prefilter was removed and discarded. 500 μl of 0.5% Tween was added and after it had passed through the membrane, 500 μl of substrate solution was added. Within 5 minutes a clear blue color appeared on that portion of the membrane coated with anti-alpha-HCG antibody, and the enzyme reaction was stopped by applying 500 μl of a 0.1% acetic acid solution to the membrane.

3. Whole blood sample reacted with enzyme conjugate prior to application to the device A 50 μl sample of HCG-containing EDTA-whole blood sample was mixed with 150 μl of enzyme conjugate, and incubated at room temperature for 1 minute. During this time the red blood cells were partially lysed. The reaction mixture was applied to the glass-fiber prefilter of the device and was drawn through an approximately 30 seconds. After an additional 2 minutes the prefilter was removed and discarded. 500 μl of 0.5% Tween was added and after it had passed through the membrane, 500 μl of substrate solution was added. Within 5 minutes a clear blue line appeared on that portion of the membrane coated with anti-alpha-HCG antibody, and the enzyme reaction was stopped by applying 500 μl of a 0.1% acetic acid solution to the membrane.

D. Assay for Infectious Mononucleosis in Whole Blood Sample

A nitrocellulose membrane having an average pore size of 5 μm (Micron Separation, Inc.) was coated with rabbit anti-goat IgG to form a horizontal bar, and was coated with purified infectious mononucleosis antigen from beef stroma to form a vertical bar crossing the horizontal bar. The coating process was performed using a Videojet ™ apparatus (an apparatus that applies droplets of liquid in a predetermined pattern on a substrate by charging the droplets in a stream and electrostatically deflecting them into a desired trajectory to form the predetermined pattern). Alkaline phosphatase conjugated goat anti-human IgM was used as enzyme conjugate.

A 50 μl sample of whole mono-positive blood (combined with heparin or EDTA as an anticoagulant) was mixed with 50 μl 2% Triton X-100 (a surfactant that lyses red blood cells) in a sample cup. After shaking briefly to thoroughly solubilize the lysis products, 50 μl of enzyme conjugated goat anti-human IgM was added to the sample cup. The resulting reaction mixture was applied to a glass fiber prefilter which was placed over the membrane, and was drawn through the prefilter and the membrane in approximately 5 seconds. The prefilter was then removed and discarded, and 500 μl of color forming enzyme substrate was added to wash visible red color from the membrane and permit color development where enzyme conjugate was bound.

The assay then proceeded on the membrane, where the enzyme conjugate had become bound by the anti-goat IgG of the horizontal bar, and infectious mononucleosis heterophile antibody in the sample had become bound to the antigen on the vertical bar. This heterophile was itself labeled with the anti-human enzyme conjugate, and within two minutes a clear blue line appeared on that portion of the membrane coated with beef stroma, indicating a positive test. The horizontal bar, which served as a positive control, also developed a blue color, so that the two bars formed a "+" symbol. (If no anti-mono antibody had been present in the sample, a "−" symbol, indicative of a negative assay, would have developed.) The reaction was stopped at that point by adding 500 μl of a 0.1% acetic acid solution to the membrane.

Under the conditions of each of the Examples, some of the red color of the blood in the samples washed through the membrane at each reagent addition step. At the time when substrate solution was added, in each case most (if not all) of the color was gone, and any remaining on the surface of the membrane did not interfere with the interpretation of the result.

Although the invention has been described in the context of a preferred embodiment, it will be understood that the invention is intended only to be limited to the lawful scope of the claims that follow, or equivalents thereof.

TABLE 1

ABILITY OF COMMERCIAL POROUS NYLON 66 MEMBRANE TO EXCLUDE ERYTHROCYTES (RBC)

| Membrane Pore Size: μm | MSI | Pall |
|---|---|---|
| 3 | | Virtually all RBC retained |
| 5 | Most RBC pass through | Very few RBC pas through |
| | Some RBC retained | Most RBC retained |
| 10 | No RBC retained | |
| 20 | No RBC retained | |

Membrane Source
MSI: Micron Separation, Inc.
Pall: Pall Corporation

What is claimed is:

1. A method for analyzing whole blood for an analyte recognized by an analyte specific reagent, comprising the steps of:
    applying whole blood to a liquid permeable support layer of an assay device, wherein said layer has said analyte specific reagent fixed thereto prior to said introduction of said blood, and wherein said whole blood is applied to said layer;
    drawing colored components of said blood through said layer; and
    forming a color on said layer in response to interaction between said analyte and said analyte specific reagent when analyte is present in said blood, thereby visually indicating on said layer the presence or absence of said analyte in said blood.

2. The method of claim 1, further comprising the step of:
    lysing red blood cells to release colored components thereof and to permit said components to be drawn through said layer.

3. The method of claim 2, wherein said lysing step is performed prior to said applying step.

4. The method of claim 2, wherein said lysing step occurs after said applying step.

5. The method of any one of claims 1-4, wherein said layer is a membrane and wherein said drawing step comprises wicking liquid components of said blood away from said membrane.

6. The method of claim 5, further comprising the steps of:
    adding a liquid to said layer after said applying step, which liquid is relatively colorless in comparison to said colored components of said blood; and
    drawing said relatively colorless liquid, together with said colored components, through said layer to enhance the visibility of color formed on said layer in said forming step.

7. The method of claim 5, wherein the membrane has an average pore size no greater than about 25 μm.

8. The method of claim 5, wherein the membrane has an average pore size no greater than about 10 μm.

9. The method of claim 5, wherein the membrane has an average pore size no greater than about 5 μm.

10. The method of claim 5, wherein said analyte comprises one member of a ligand-antiligand pair and said analyte specific reagent comprises the other member of said ligand-antiligand pair.

11. The method of claim 10, wherein said ligand-antiligand pair comprises an antigen and an antibody.

12. The method of claim 1, wherein said color change occurs as a result of the action of an enzyme on a substrate, which enzyme is immobilized on said membrane at the time of said color change.

13. The method of claim 1, wherein said analyte and said analyte specific reagent together comprise an enzyme-substrate pair.

14. The method of claim 1, wherein said drawing step comprises drawing hemoglobin from lysed red blood cells through said layer.

15. The method of claim 1, wherein said drawing step comprises drawing whole red blood cells through said layer.

16. The method of claim 1-4, comprising an assay for infectious mononucleosis.

17. The method of claim 16, wherein the analyte specific reagent is mononucleosis antigen and said analyte is infectious mononucleosis heterophile antibody.

* * * * *